(12) United States Patent
Abele et al.

(10) Patent No.: US 8,029,434 B2
(45) Date of Patent: Oct. 4, 2011

(54) DEVICE FOR THE PREVENTION OF INCONTINENCE, ESPECIALLY URINARY INCONTINENCE

(75) Inventors: Wolfgang Abele, Tuttlingen/Donau (DE); Erich K. Odermatt, Schaffhausen (CH)

(73) Assignee: Aesculap AG, Tuttlingen/Donau (DE)

( * ) Notice: Subject to any disclaimer, the term of this patent is extended or adjusted under 35 U.S.C. 154(b) by 144 days.

(21) Appl. No.: 11/919,824

(22) PCT Filed: May 4, 2006

(86) PCT No.: PCT/EP2006/004175
§ 371 (c)(1), (2), (4) Date: Jan. 16, 2008

(87) PCT Pub. No.: WO2006/117214
PCT Pub. Date: Nov. 9, 2006

(65) Prior Publication Data
US 2009/0023979 A1     Jan. 22, 2009

(30) Foreign Application Priority Data
May 4, 2005    (DE) .................. 10 2005 021 881

(51) Int. Cl.
*A61F 2/02* (2006.01)
(52) U.S. Cl. ............... 600/30; 128/DIG. 25; 600/37
(58) Field of Classification Search ............ 600/29–32, 600/37; 604/95.03, 509; 623/7, 8, 14.13, 623/23.64, 23.66, 23.67
See application file for complete search history.

(56) References Cited

U.S. PATENT DOCUMENTS

| | | | |
|---|---|---|---|
| 3,789,828 A | 2/1974 | Schulte | |
| 4,634,443 A | 1/1987 | Haber | |
| 5,634,877 A | 6/1997 | Salama | |
| 6,786,861 B1 | 9/2004 | Pretorius | |
| 6,911,002 B2 | 6/2005 | Fierro | |
| 7,395,822 B1* | 7/2008 | Burton et al. ............... | 128/885 |
| 2002/0183588 A1 | 12/2002 | Fierro | |
| 2004/0013873 A1* | 1/2004 | Wendorff et al. ........... | 428/364 |
| 2004/0215054 A1* | 10/2004 | Siegel et al. ................. | 600/31 |
| 2004/0230316 A1 | 11/2004 | Cioanta et al. | |
| 2004/0249240 A1 | 12/2004 | Goldmann et al. | |
| 2005/0038380 A1 | 2/2005 | Nemir et al. | |
| 2005/0283040 A1* | 12/2005 | Greenhalgh .................. | 600/30 |

FOREIGN PATENT DOCUMENTS

| | | |
|---|---|---|
| DE | 43 28 158 A1 | 2/1996 |
| DE | 100 13 519 A1 | 10/2001 |
| DE | 202 04 669 U1 | 9/2003 |
| EP | 0 858 299 B1 | 8/1998 |
| FR | 2 802 798 A1 | 6/2001 |
| WO | 00/66030 A1 | 11/2000 |
| WO | 01/26581 A1 | 4/2001 |
| WO | 01/45589 A1 | 6/2001 |

* cited by examiner

*Primary Examiner* — Charles A Marmor, II
*Assistant Examiner* — Carrie R Dorna
(74) *Attorney, Agent, or Firm* — The Nath Law Group; Jerald L. Meyer; Stanley N. Protigal

(57) ABSTRACT

The invention relates to a device for the prevention of incontinence, especially urinary incontinence, with an expandable balloon (3) that is connected to at least one fluid conduit (6) by means of which the volume of the balloon (3) can be adjusted. The band is embodied as a porous tube (1). The balloon (3) is located inside the porous tube.

21 Claims, 2 Drawing Sheets

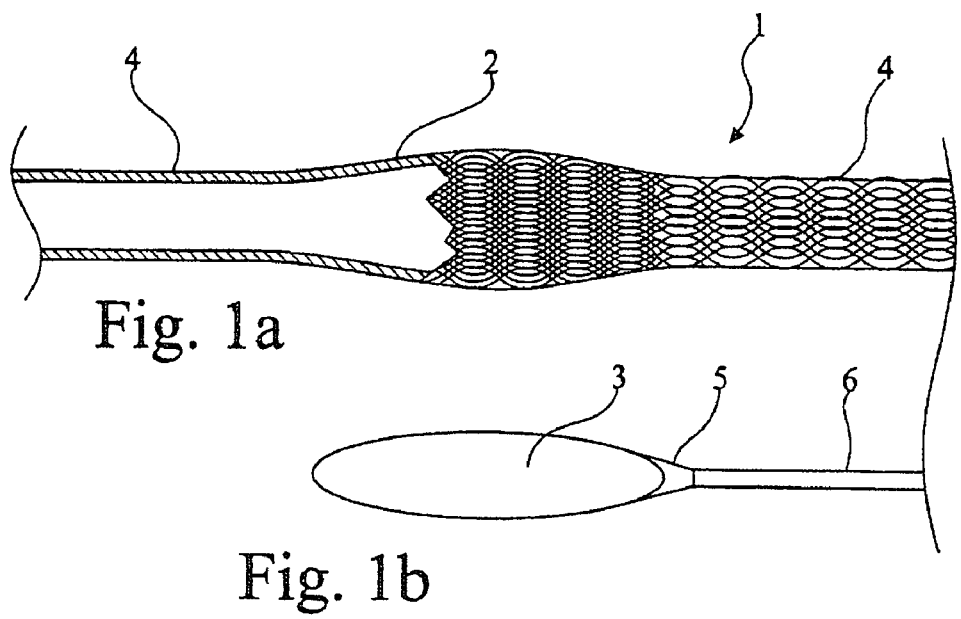
Fig. 1a
Fig. 1b
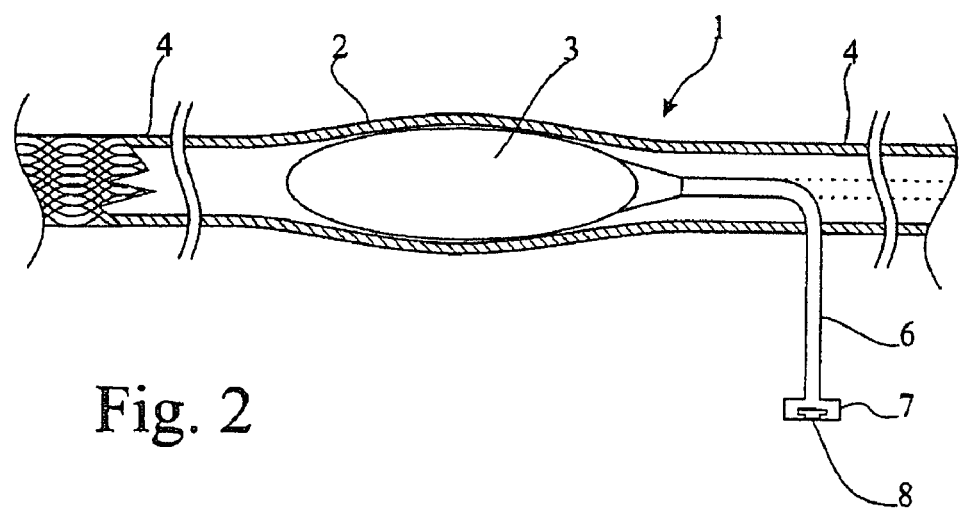
Fig. 2

DEVICE FOR THE PREVENTION OF INCONTINENCE, ESPECIALLY URINARY INCONTINENCE

The invention relates to a device for the prevention of incontinence, especially urinary incontinence, with an expandable balloon which, upon implantation, comes to lie in the area of the urethra and is able to lift and/or compress the urethra so as to prevent incontinence.

Many urinary incontinence bands with an expandable balloon are known. Reference is made to DE 43 28 158 A1, O 00/18319, WO 00/66030 and WO 03/013392 A1. In the known urinary incontinence bands, the balloon is generally made of silicone. Silicone is a material which is biocompatible, can be suitably shaped and can be connected, for example by adhesion, to supply lines. However, it has been found that silicone may lead to erosion of the urethra after prolonged implantation.

The object of the invention is therefore to make available a device for the prevention of incontinence, with an expandable balloon in which such erosion is avoided.

The subject matter of the invention is a device for the prevention of incontinence, especially urinary incontinence, with an expandable balloon that is connected to at least one fluid conduit by means of which the volume of the balloon can be adjusted, wherein the balloon is located inside a porous tube. The subject matter of the invention serves primarily for the prevention of male and female urinary incontinence. The subject matter of the invention can also be used for fecal incontinence.

WO 01/26581 A1 discloses an implant for the treatment of urinary incontinence, in which an expandable balloon is arranged in a tubular sleeve. However, this sleeve serves only as an insertion aid during implantation and is removed again after the balloon has been implanted.

It has been found that erosion of the urethra can be avoided by permanently enveloping the balloon in the porous tube. Silicone is a material that does not form adhesive connections within the body. This is attributed, on the one hand, to the surface properties of the silicone and, on the other hand, to the fact that silicone has a closed surface. By contrast, a porous tube can connect firmly to the body tissue by means of cells of the connective tissue growing into the pores and connecting firmly to the material of the tube. In this way, the urethra is covered by scar tissue, which is strengthened by the porous tube material. This means that relative movements between the balloon and the urethra can no longer lead to wearing through of the urethra. The tube material can be connected to the balloon, for example adhesively connected. It may also be preferable, however, to provide no connection between the balloon and the tube, such that a relative movement between the balloon and the tube still remains possible after the implantation, which may be necessary for the wellbeing of the patient when moving.

Suitable porous tubes are ones that are known, for example, as vascular prostheses. They can be made of expanded polytetrafluoroethylene, or also of polyurethane which is shaped into a tube from dissolved polyurethane by spray technology.

Textile tubes are particularly suitable. It is possible to use woven tubes and, in particular, tubes made from formed-loop or drawn-loop knits. These have many applications in vascular prosthetics. The size of the pores must be at least large enough to allow connective tissue to migrate into the pores. The pores are preferably >20 µm, in particular >100 µm. The pores are, on the other hand, sufficiently small to prevent contact of the urethra by the balloon.

Particular preference is given to porous tubes with a net structure, in which the pores are substantially larger, preferably in the range of 0.8 to 3 mm. In addition to the looped fabrics, other suitable textile materials are tubular braids.

In a preferred embodiment of the invention, the porous tube, at least in the area of the balloon, is elastically expandable in diameter. Formed-loop knits, drawn-loop knits and braids are particularly suitable for this embodiment. The tube advantageously has a greater diameter in the area of the balloon than it does in the areas outside the balloon. This greater diameter can be predetermined or obtained by the elastic expandability. The balloon is also advantageously fixed inside the tube in the longitudinal direction thereof. Such fixing can be achieved by a narrowing of the tube outside the area of the balloon.

In a preferred embodiment, the tube has smaller pores in the area of the balloon than it does outside this area. The small pores have the effect that contact of the balloon material with the urethra is avoided. This problem does not arise outside the area of the balloon. Accordingly, the mesh width or pore aperture of the tube can be kept very large there, for example as much as 5 mm, as a result of which rapid union with the connective tissue is achieved, such that special means of fixing the band-shaped tube to parts of the body, for example to bone, can be dispensed with.

Particularly suitable materials for a textile tube are polyvinylidene fluoride (PVDF) or polypropylene or a mixture thereof, particularly in monofilament form. For specific applications, the textile tube, at least in the central area, can also comprise or consist of multifilament threads, especially velour threads. This permits particularly rapid and secure union with the connective tissue. The tube can be produced from flat material and have a longitudinal seam. It is preferably produced as a seamless tubular material. In order to control the formation of the scar tissue around the tube not only by way of the pore size, the weight per unit of area of the tube, in particular of the textile tube, can also be adapted, from 12 to 120 g/m$^2$. The thinner the textile tube, the less the scar tissue that forms. However, even with a thicker scar tissue cover, the pressure of the balloon can still expand the scar tissue if allowed to act on it for sufficient time.

The wall of the balloon inside the tube can be doubled and can unfold as the balloon is filled with fluid. Generally, an elastic expandability of the balloon wall is sufficient. The balloon and preferably also the at least one supply conduit are therefore advantageously made in a manner known per se from silicone.

The at least one conduit preferably extends along the tube and is preferably routed at least as far as the end of the tube. In another embodiment, it is possible for the at least one conduit, between the balloon and an end of the tube, to be routed radially out of the tube through the wall of the latter. In this embodiment, the end of the conduit can be positioned independently of the end of the tube. The free end of the conduit is advantageously closed in a manner known per se with a fluid valve, for example with a pierceable septum. During the implantation, this valve is fixed on an area of the body accessible from the outside.

The balloon normally has an elongate shape with circular cross section. If so desired, the balloon can also be given a special shape. Thus, the tube and/or the balloon, in the area that comes to lie near the urethra upon implantation, can be narrowed or adopt a U-shape, for example. The wall thickness of the balloon can also be varied.

The tube is preferably designed as a band which protrudes beyond the balloon at both ends. This allows the device according to the invention to be implanted in the usual way as a urinary incontinence band. In a preferred embodiment of the invention, the band protrudes beyond the balloon only at one end. Provision can be made here for the tube to be closed at least at one end and for the balloon to be located at an end. This embodiment permits minimally invasive implantation through just one surgical incision. It is even possible to design the tube simply as a sleeve which, in terms of its size, corresponds substantially to that of the balloon.

In preferred embodiments, the tube is provided with an adhesive, in particular with a biological adhesive. Fibrinogen and thrombin are in particular suitable for this purpose. This adhesive provides preliminary fixing in the body until the porous tube has become incorporated.

Further features of the invention will become clear from the following description of preferred embodiments of the invention in conjunction with the dependent claims and the drawing. Here, the individual features can each be realized singly or severally in an embodiment of the invention.

In the drawing:

FIG. 1a shows a longitudinal view of an embodiment with the porous tube,

FIG. 1b shows a balloon with supply line for arrangement inside the tube,

FIG. 2 shows a schematic longitudinal section of the tube within which the balloon is arranged.

Figure 3:
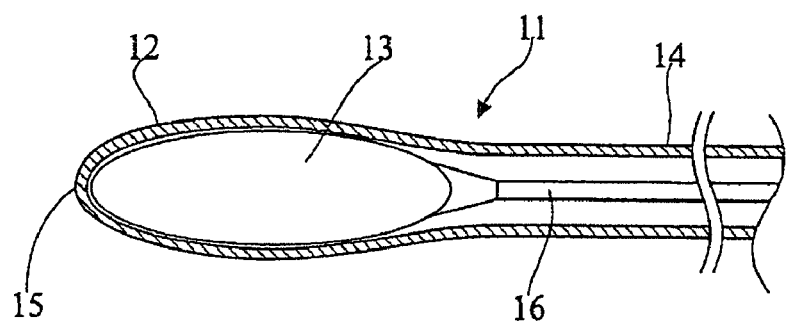
FIG. 3 shows another embodiment.

In the embodiment of the invention shown schematically in the drawing in FIGS. 1a and 1b, a tube 1 made from a formed-loop knit and with a length of ca. 50 cm is provided. The tube has a central portion 2, which is provided for receiving a balloon 3. The central portion has a diameter of ca. 25 mm, which is approximately twice as great as the diameter of the tubular side portions 4 adjoining the central portion 2 at both ends. The side portions 4 each have a length of 20 cm. The tube 1 is produced in the form of an extensible circular formed-loop knit made up of monofilament polypropylene. The circular formed-loop knit is net-like and has a clear pore width of ca. 4 mm in the side portions and of ca. 0.8 mm in the central portion 2. The central portion has a length of ca. 10 cm.

The balloon 3 shown in FIG. 1b has a length of once again ca. 10 cm and, without the envelope, can be expanded by the tube up to a maximum diameter of ca. 40 mm, which corresponds to a maximum volume of ca. 125 ml. A volume of 5 to 25 ml is usually sufficient. At one end 5, a silicone tube 6, which is likewise sealingly affixed to the balloon made of silicone, opens into the balloon 3. The balloon and tube can also be composed of soft, elastic polyurethane.

In the embodiment according to FIG. 2, the balloon 3 is already located in the central portion 2 of the tube 1. The silicone tube 6 first extends by a certain distance through a side portion 4 of the tube 1 and is then routed radially outward through the wall of the tube 1. As will be seen from the broken lines, the silicone tube 6 can also extend inside the tubular side portion 4 as far as the end thereof or indeed beyond this. A valve 7 is connected to the free end of the silicone tube 6. This valve 7 has a pierceable septum 8. With the aid of a syringe needle, fluid, generally a liquid, can be introduced into the balloon by way of the silicone tube serving as supply line. After implantation, the balloon can be adjusted to the correct degree of filling via the valve 7.

After implantation, a scar tissue, which grows fixedly onto the net tube 1, forms between the central portion 2 of the tube 1 and the connective tissue surrounding the urethra. Relative movements between the balloon 3 of silicone and the inner surface of the central portion 2 of the band 1 do not exert an action on the urethra, because the scar tissue, which is strengthened by the net material of the tube, constitutes a mechanical guard.

Since the formed-loop knit composed of monofilament threads is elastically extensible, the central portion can widen elastically to a certain degree, upon filling of the balloon 3, and can participate in the movement of the balloon. When the extensibility reaches its limit value, further filling of the balloon leads to a substantial increase in pressure, with the result that it is easy to detect when the maximum degree of filling is reached.

In the embodiment according to FIG. 3, a tube 11 is designed as a blind tube. A balloon 13 is located at one end of the blind tube 12 corresponding to the central portion 2 of FIG. 2, but is closed at one end 15. This end 15 closes the balloon 13 at one side. For implantation of this embodiment, only one area of the body has to be opened in order to introduce the balloon. Primary fixing of the balloon in the area of the urethra can be effected by means of an adhesive, for which purpose a so-called fibrin adhesive is suitable. Suitable biological adhesives are, for example, fibrinogen and thrombin.

A silicone tube 16 with valve and septum can be designed in the same way as in the embodiments according to FIGS. 1 and 2 and either routed through the wall of the tube portion 14 or routed along this tube.

Figure 4:
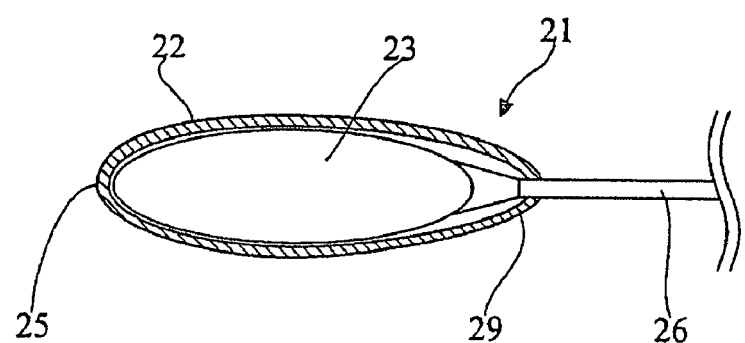
FIG. 4 shows a further embodiment.

In the embodiment according to FIG. 4, a tube 21 is designed as a sleeve for the balloon 23 and surrounds the balloon 23 in the manner of a cushion cover 22. Ends 25 and 29 of the tube 21 are closed, except for a silicone tube 26 which is routed through the end 29 and in turn has a valve with a septum.

This embodiment too is suitable for minimally invasive implantation with only one incision site. The initial fixing of the enveloped balloon can in turn take place with the aid of biological adhesives. The final fixing takes place as a result of connective tissue growing into the porous tube 21.

The materials used, in particular the material of the tube and of the balloon and of the supply line, can be provided with antimicrobial substances, which are located in the materials and/or on the surface thereof. In this way, it is possible to prevent infections resulting from the implantation or even infections that occur later on. It is also possible in a manner known per se to provide the different parts of the urinary incontinence band with markers which can be detected by physical methods such as radiography or ultrasound and the like. In this way, it is possible to adjust and monitor the correct position of the urinary incontinence band in the body during the implantation and also subsequently.

The implant can be implanted using a minimally invasive operating procedure analogous to the transobturator technique (TOT) in female urinary incontinence or by another minimally invasive operating technique from the field of female urinary incontinence. Other alternative access routes from below are also possible, for example access from the region of the perineum or the region of the os pubis, for placement of the implant by a minimally invasive approach. The implant can be placed above or below the urethra, the minimally invasive access route being chosen accordingly. Placement of the balloon above the urethra is the preferred implantation method in urinary incontinence. To prevent fecal incontinence, the device is implanted in the region of the sphincter muscle.

The invention claimed is:

1. A device for the prevention of incontinence, comprising:
   an expandable balloon that is connected to at least one fluid conduit by means of which the volume of the balloon can be adjusted, wherein the balloon is located inside a porous tube in an abutting configuration in a closed end of the tube with a second open end of the tube extending beyond the balloon in a non-abutting configuration, the tube designed as a band which protrudes beyond the balloon at said second open end.

2. The device as claimed in claim 1, wherein the tube is a textile tube.

3. The device as claimed in claim 1, wherein the textile tube has a net structure.

4. The device as claimed in claim 1, wherein the tube is made from a looped fabric.

5. The device as claimed in claim 1, wherein the tube is a tubular braid.

6. The device as claimed in claim 1, wherein the tube, at least in the area of the balloon, is elastically expandable in diameter.

7. The device as claimed in claim 1, wherein the tube has a greater diameter in the area of the balloon than it does in the areas outside the balloon.

8. The device as claimed in claim 1, wherein the balloon is fixed in the tube against displacement in the longitudinal direction of the tube.

9. The device as claimed in claim 1, wherein the tube has smaller pores in the area of the balloon than it does outside this area.

10. The device as claimed in claim 1, wherein the textile tube is made of a material selected from the group consisting of PVDF, polypropylene, and combinations thereof.

11. The device as claimed in claim 1, wherein the tube is produced from monofilament threads.

12. The device as claimed in claim 1, wherein the balloon is elastically expandable.

13. The device as claimed in claim 1, wherein the balloon and also the at least one fluid conduit are made of silicone.

14. The device as claimed in claim 1, wherein at least one fluid conduit is routed along the inside of the tube, at least as far as the end of the tube.

15. The device as claimed in claim 1, wherein at least one fluid conduit between the balloon and an end of the tube is routed radially out of the tube through the wall of the latter.

16. The device as claimed in claim 1, wherein a free end of the fluid conduit is closed with a fluid valve.

17. The device as claimed in claim 1, wherein the tube is closed at at least one end and the balloon is located at this end.

18. The device as claimed in claim 1, wherein the tube is closed at both ends and its length corresponds substantially to that of the balloon.

19. The device as claimed in claim 1, wherein the tube is provided with an adhesive.

20. The device as claimed in claim 1, wherein the tube is made from a formed-loop knit or drawn-loop knit.

21. The device as claimed in claim 1, wherein the tube in the area of the balloon is provided with an adhesive.

* * * * *